United States Patent [19]
Tenzel et al.

[11] Patent Number: 5,000,887
[45] Date of Patent: * Mar. 19, 1991

[54] PREPARATION OF UNIFORM-SIZE LIPOSOMES

[75] Inventors: Renée A. Tenzel, Mountain View; David F. Aitcheson, San Jose, both of Calif.

[73] Assignee: Liposome Technology, Inc., Menlo Park, Calif.

[*] Notice: The portion of the term of this patent subsequent to Feb..19, 2008 has been disclaimed.

[21] Appl. No.: 194,856

[22] Filed: May 17, 1988

[51] Int. Cl.$^5$ ............ A61K 9/133; A61K 9/127; B01J 13/12
[52] U.S. Cl. ............ 264/4.6; 264/4.1; 424/450
[58] Field of Search ............ 424/450; 428/402.2; 264/4.3, 4.6, 4.1

[56] References Cited

U.S. PATENT DOCUMENTS

| | | | |
|---|---|---|---|
| 4,235,871 | 11/1980 | Papahadjopoulos et al. | 264/4.6 |
| 4,438,052 | 3/1984 | Weder et al. | 264/4.6 |
| 4,608,211 | 8/1986 | Handjani et al. | 264/4.6 |
| 4,731,210 | 3/1988 | Weder et al. | 264/4.3 |
| 4,781,871 | 11/1988 | West, III et al. | 264/4.3 |

FOREIGN PATENT DOCUMENTS 0055576 7/1982 European Pat. Off.
0158441 10/1985 European Pat. Off. ............ 424/450

OTHER PUBLICATIONS

Batzri et al., "Single Bilayer Liposomes...", *Biochim Biophys. Acta*, vol. 298, pp. 1015–1019, 1973.
Kremer et al., "Vesicles of Variable Diameter...", *Biochemistry*, vol. 16, No. 17, pp. 3932–3935, 1977.

*Primary Examiner*—Richard D. Lovering
*Assistant Examiner*—John M. Covert
*Attorney, Agent, or Firm*—Peter J. Dehlinger

[57] ABSTRACT

A method of forming liposomes with a uniform size distribution, and an average size of about 300 nm or less. Vesicles-forming lipids are dissolved in a water-miscible solvent, such as ethanol, and an aqueous medium is added to a water:solvent ratio at which lipid assembly first occurs. The water:solvent ratio is raised, under conditions which maintain the volume of the mixture substantially constant, until uniform-size liposomes are formed. The average size of the liposomes can be selectively varied by changing the ionic strength and lipid composition of the mixture. In one embodiment, the method is used to produce small unilamellar vesicles. Also disclosed are suspensions of liposomes which have a narrow, substantially symmetrical size distribution in a selected size range.

6 Claims, 5 Drawing Sheets

PREPARATION OF UNIFORM-SIZE LIPOSOMES

FIELD OF THE INVENTION

The present invention relates to a method of preparing uniform-size liposomes, and in particular, uniform-size liposomes having a selected mean diameter less than about 300 nm.

REFERENCES

Gregoriadis, G., in Liposomes , vol. III.
Poznansky, M. L., et al, Pharm Revs, 36(4):277 (1984).
Szoka, F., et al, Proc Nat Acad Sci (USA), 75:4194 (1978).
Szoka, F., et al, Ann Rev Biophys Bioeng, 9:467 (1980).

BACKGROUND OF THE INVENTION

The use of liposomes for drug delivery has been widely proposed. Liposomes have the potential for providing controlled "depot" release of an administered drug over an extended time period, and of reducing the side effects of the drug, by limiting the concentration of free drug in the bloodstream. These advantages of liposome drug delivery apply to a variety of routes of administration, including intravenous, intramuscular, and subcutaneous, application to mucosal tissue, or delivery by inhalation. Where liposomes are administered by intravenous delivery, liposomes provide a further advantage of altering the tissue distribution of the drug. Liposome drug delivery systems have been reviewed (Poznansky, Gregoriadis).

Generally, the optimal liposome size for use in parenteral administration is between about 100 nm and 300 nm. Liposomes in this size range can be sterilized by passage through conventional filters having a particle size discrimination of about 200 nm. This size range of liposomes also favors biodistribution in certain target organs, such as liver, spleen, and bone marrow (Gabizon), and gives more uniform and predictable drug-release rates and stability in the bloodstream. Liposomes whose sizes are less than about 300 nm also show less tendency to agglutinate on storage, and are thus generally safer and less toxic in parenteral use than larger-size liposomes. Uniform-size liposomes in a selected size range less than about 100 nm, are also useful in therapeutic applications. For example, small unilamellar vesicles (SUVs) having sizes between about 30–80 nm are useful in targeting to tumor tissue or to hepatocyte cells, because of their ability to penetrate the endothelial lining of capillaries. SUVs are also advantageous in ophthalmic liposome formulations, because of the greater optical clarity of the smaller liposomes.

A variety of techniques for preparing liposomes have been proposed (Szoka 1983). Typically, these methods yield liposomes which are heterodisperse, and predominantly greater than about 1 micron (1,000 nm) in size. These initial heterodispersed suspensions can be reduced in size and size distribution by a number of known methods. One size-processing method which is suitable for large-scale production is homogenization. Here an initial heterodispersed liposome preparation is pumped under high pressure through a small orifice or reaction tank. The suspension is usually cycled through the reaction tank until a desired average size of liposome particles is achieved. A limitation of this method is that the liposome size distribution is typically quite broad and variable, depending on a number of process variables, such as pressure, number of homogenization cycles, and internal temperature. Also, the processed fluid tends to pick up metal and oil contaminants from the homogenizer pump, and may be further contaminated by residual chemical agents used to sterilize the pump seals.

Sonication, or ultrasonic irradiation, is another method that is used for reducing liposome sizes by shearing, and is especially useful for preparing SUVs. The processing capacity of this method is quite limited, since long-term sonication of relatively small volumes is required. Also, localized heat build-up during sonication can lead to peroxidative damage to the lipids, and sonic probes shed titanium particles which are potentially quite toxic in vivo.

A third general size-processing method known in the prior art is based on liposome extrusion through uniform pore-size polycarbonate membranes (Szoka 1978). This procedure has advantages over homogenization and sonication methods in that several membrane pore sizes are available for producing liposomes in different selected size ranges. In addition, the size distribution of the liposomes can be made quite narrow, particularly by cycling the material through the selected-size filter several times. Nonetheless, the membrane extrusion method has limitations in large-scale processing, including problems of membrane clogging, membrane fragility, and relatively slow throughput Co-owned U.S. Pat. No. 4,737,323 for "Liposome Extrusion Method" describes a liposome sizing method in which heterogeneous-size liposomes are sized by extrusion through an asymmetric ceramic filter. This method allows greater throughput rates, and avoids problems of clogging since high extrusion pressure and reverse-direction flow can be employed. However, like the membrane extrusion method, the filter-extrusion method requires post-liposome formation sizing. Further, the method may be limited where uniform-size SUVs are desired.

In none of the methods mentioned above, are liposomes with a narrow, symmetrical size distribution produced.

SUMMARY OF THE INVENTION

It is a general object of the invention to provide an improved method of preparing uniform size liposomes having an mean diameter less than about 300 nm, without requiring post-liposome formation extrusion or other sizing procedures.

Another object is to provide such a method which can be used to produce uniform-size liposomes having a selected mean diameter between about 30–300 nm.

Still another object of the invention is to provide such a method which can be practiced to achieve relatively high encapsulation rates, and in which loss of non-encapsulated material is avoided.

Still another object of the invention is to provide a novel liposome preparation having a narrow, substantially symmetrical size distribution of liposomes with a selected mean diameter of between about 30–300 mm.

The invention includes, in one aspect, a method of forming a suspension of liposomes having a substantially uniform size distribution. There is first formed a mixture of vesicle-forming lipids in a single-phase solvent system containing a water-miscible lipid solvent and water. The water:solvent ratio of the mixture is raised to a point at which lipid assembly first occurs, as evidenced by the formation of microscopically visible, amorphous lipid structures. The water:solvent ratio of the mixture is then increased, under conditions which maintain the volume of the mixture substantially constant, until uniform-size liposomes are produced.

According to another aspect of the invention, the average liposome size which is produced can vary from about 30–300 nm, according to lipid composition and ionic strength of the mixture during liposome formation. By way of example, SUVs are formed with neutral lipid components, and with lipid components containing 5–10 mole percent negatively charged phospholipid at low ionic strength. Liposomes with average sizes about 250 nm are formed with lipid components containing 5–10 mole percent negatively charged phospholipid at higher ionic strength.

In one preferred embodiment of the method, the water:solvent ratio is raised in a reverse osmosis system in which solvent and water are removed by reverse osmosis, and an aqueous medium is added at a rate which balances solvent/water loss.

In another embodiment, the ratio of water:solvent in the mixture is raised in a solvent evaporation system in which solvent is preferentially evaporated, under pressure and temperature conditions which allow for removal of the solvent, while aqueous medium is introduced at a rate that balances the volume loss by evaporation.

The invention also includes a unique method for producing SUVs without high shear down-sizing of previously formed liposomes.

In another aspect, the invention includes a suspension of liposomes having a mean diameter in a selected size range between about 30–300 nm, and a narrow, substantially symmetrical size distribution.

These and other objects and features of the invention will become more fully appreciated when the following detailed description of the invention is read in conjunction with the accompanying drawings.

DETAILED DESCRIPTION OF THE INVENTION

A. Lipid/Solvent/Water Mixture

Figure 1:
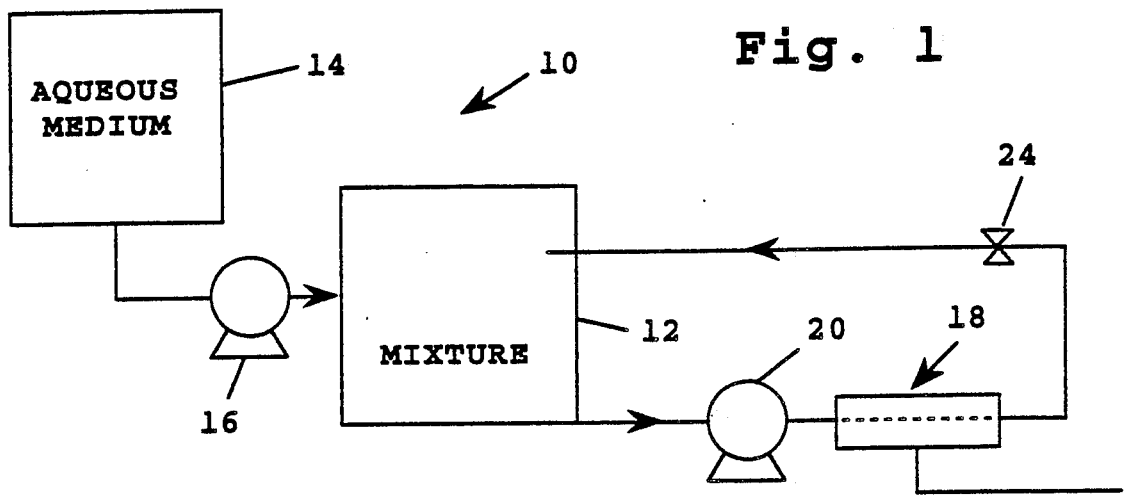
FIG. 1 is a schematic drawing of a reverse osmosis system used in practicing the present invention according to one embodiment.

The lipid/solvent/water mixture formed in practicing the invention is composed of vesicle-forming lipids, a water-miscible lipid solvent, an aqueous medium, which preferably includes charged solute components. The mixture is brought to a water:solvent ratio at which formation or assembly of amorphous lipid structures first occurs.

The vesicle-forming lipids in the mixture generally include neutral and negatively charged phospholipids, such as phosphatidylcholine (PC) and phosphatidylglycerol (PG). The lipids may also include sterol lipids, such as cholesterol, and/or glycolipids, such phosphatidylinositol, gangliosides, and the like. A variety of lipids having selected acyl chain compositions are commercially available or may be obtained by standard lipid isolation procedures.

One factor in the choice of lipid components in the mixture is the size-effect of charged lipid species. For example, egg PC (with no charged lipid) produces uniform-size liposomes having a mean diameter of about 30–60 nm. By contrast, a lipid composition containing egg PC and 5% egg PG produces a liposome mean diameter which is dependent on ionic strength (Example 1 and 2).

The water-miscible lipid solvent used in the mixture is defined herein as one which can be mixed with an aqueous medium in substantially any proportion without forming a two-phase system. Preferred solvents are small alcohols, such as ethanol, methanol, propanol, and isopropanol, dimethylsulfoxide (all suitable for reverse osmosis), and small dimethoxy and diethoxy compounds, such as dimethoxy methane and dimethoxyethane (also suitable for solvent evaporation).

The solvent may contain additional solvent components, such as chloroform, acetone, or chlorofluorocarbon solvents, which are typically added to increase lipid solubility, and are present at a sufficiently low concentrations that solvent phase separation does not occur. For example, one suitable solvent for preparing liposomes containing phospholipid and cholesterol components contains ethanol as primary solvent component and between about 10%–20% chlorofluorocarbon solvent.

As indicated above, the ionic strength of the mixture during liposome formation may determine liposome mean diameter, when charged lipid components are present. As seen in Examples 1 and 2, a relatively low ionic strength results in liposomes less than about 50 nm, whereas at a tenfold higher ionic strength, a liposome in the 200–300 nm range are produced. The ionic component of the mixture is typically provided by a salt, such as sodium or potassium chloride or phosphate salts, which is preferably added as an aqueous salt or buffer solution to the lipid solvent. Alternatively, the ionic component may include a charged compound which is to be encapsulated or entrapped in liposomes. For forming SUVs with a mean diameter of less than about 50 nm, and with charged lipid components, the ionic strength of the medium during liposome formation is typically less than about 30 mM, and preferably between about 5-20 mM. Alternatively, where neutral lipid components alone are used, the size of the liposomes is relatively independent of ionic strength.

In preparing the lipid/solvent/water mixture, the selected lipids are preferably first dissolved in the lipid solvent. The amount of lipid added is calculated to give a final lipid concentration in the mixture between 10-600 um/ml, and preferably between about 100-300 um/ml, depending on desired final lipid concentration, encapsulation efficiency, and method of solvent removal. One advantage of solvent removal by evaporation is that higher lipid concentrations (above about 300 um/ml may be employed. The lipid solution may also include lipophilic drug components which are to be entrapped in the liposomes. After dissolution of the lipid components, aqueous medium is added to a final water:solvent ratio at which lipid assembly first occurs. The aqueous medium used in forming the final lipid/solvent/water mixture may include salts or other ionic species and water-soluble drug compounds which are to be encapsulated in the liposomes.

The aqueous medium may be added to the lipid/solvent solution by dilution and/or under conditions in which addition of aqueous medium is balanced by removal of solvent, i.e., where the volume of the medium is substantially constant. The procedure described in Examples 1 and 2 is illustrative. Here an initial lipid in ethanol solution is diluted with distilled water to a final water:solvent volume ratio of about 1:9. Additional aqueous medium is then added in a reverse osmosis system (described in Section B below) by addition of a buffer containing the desired salt concentration, under conditions in which the volume of the mixture is maintained substantially constant, i.e., where addition of aqueous medium is balanced by removal of solvent and water.

As the water:solvent volume ratio of the mixture is increased, the mixture typically becomes translucent. With continued replacement of solvent by water (or dilution with water), lipid assembly begins to occur, as evidenced by the appearance of large vesicular structures as well as amorphous lipid bodies (as observed by light microscopy). In the case of ethanol, the solvent ratio at which lipids first form or assemble is typically between about 40%-55%, depending on lipid concentration and percent charged lipid components. Experiments conducted in support of the present invention show that the lipid structure formation occurs at about 56% ethanol for uncharged lipid components, and falls to about 40% ethanol as the percent negatively charged lipid is increased to about 30 mole percent.

In another embodiment, the lipid/solvent/mixture is brought to the desired water:solvent volume ratio by preferential solvent removal under pressure and temperature conditions which allow for removal of the solvent, with addition of aqueous medium to balance solvent loss. An aqueous injection system for producing the mixture is described in Section C. As with the reverse osmosis approach, the lipid solvent may be initially diluted with water or ionic solution, then carried to the desired water:solvent volume ratio under substantially constant-volume conditions.

Other methods of solvent removal, under conditions which preserve a substantially equal lipid-mixture volume, are also possible. For example, the solvent in the mixture can be removed by preferential binding to or inclusion in a solid matrix or substrate, as the total volume of the mixture is maintained by introduction of aqueous medium.

Alternatively, solvent can be removed preferentially from the mixture by contact with an organic solvent which is (a) immiscible with water, (b) miscible with the lipid solvent, and (c) itself a poor solvent for lipid. As an example, a lipid mixture of containing lipid in dimethylsulfoxide (DMSO) and water can be gradually depleted of DMSO by contact with a selected fluorochlorocarbon solvent, having a low solubility for the vesicle-forming lipids in the mixture. Solvent depletion is balanced in such a two-phase system by addition of aqueous medium to maintain the aqueous-phase volume substantially constant.

B. Solvent Exchange by Reverse Osmosis

FIG. 1 shows a reverse osmosis (RO) system 10 designed for solvent exchange in a liposome preparation method. The system includes a holding tank 12 and a vessel 14 which feeds aqueous medium to the tank, at a controlled rate, via a pump 16. In a specific embodiment of the invention, where the volume of the mixture in the tank is maintained at about 1 liter, the pump is operated to supply medium to the tank at between about 5-200 ml/min, preferably 20-80 ml/min, and the pumping rate is preferably controlled to match the rate of removal of liquid from the tank by RO filtration.

A crossflow RO filter 18 is connected to the tank through a high pressure pump 20 which circulates the fluid in the tank in the direction shown. The speed of the pump is adjustable to regulate the rate of fluid flow through the filter. The flow rate is typically set to about 80% of maximum. A valve 24 is adjustable to control the pressure within the filtration device. Typically the filtration pressure is between about 400-600 psi.

Filter 18 is selected on the basis of ability to pass the solvent(s) in the lipid/solvent/water mixture. RO filters designed for passage of a variety of small, water-miscible solvents are commercially available, such as from Millipore Corporation (Bedford, Mass.).

In operation, a given volume of lipid/solvent or lipid/solvent/water mixture is added to the tank. In a preferred embodiment, the water:solvent ratio in the initial mixture is substantially less than that at which lipid assembly first occurs. That is, the RO system is used to raise the water:solvent ratio to the lipid assembly point, as well as during liposome formation following initial lipid assembly, under constant-volume conditions.

The aqueous medium stored in vessel 14 preferably contains larger molecular weight solute molecules to be encapsulated in the liposomes, and salt or other ionic species added to control liposome size. If the compound to be encapsulated is contained in the first portion of aqueous medium, the total volume of the first portion of aqueous medium preferably should be no greater than that required to bring the mixture in the tank to the point of lipid assembly. In the method illustrated in Examples 1 and 2, where the first aqueous volume contains the ionic species in the mixture, but not drug solute molecules, the first aqueous medium and the initial mixture in the tank both have the same 1 liter volume. Four additional volumes of distilled water are added subsequently, to remove all but residual amounts of the solvent from the liposome preparation.

Figure 2:
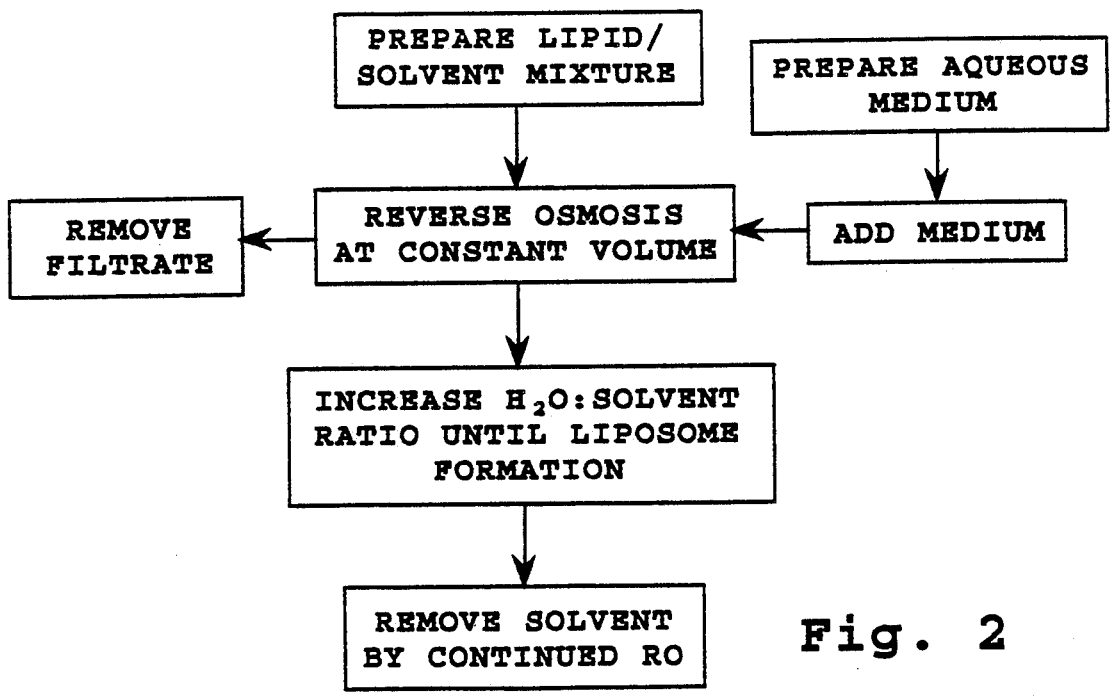
FIG. 2 is a flow diagram of the steps used in practicing the method of the invention using reverse osmosis.

FIG. 2 is a flow diagram of the processing steps in the RO method. The reverse osmosis step in the diagram involves circulating the tank mixture under pressure across an RO membrane, with addition of aqueous medium from vessel 14 to balance solvent/water RO filtrate loss. As the water:solvent ratio in the tank is raised, the mixture will reach that water:solvent ratio at which lipid assembly first occurs, i.e., the lipid/solvent/water mixture described in Section A will be formed. With continued solvent exchange, the mixture passes through the stage where smaller lipid aggregates are observed, followed by a final reformation producing uniform-size liposomes having the desired mean diameter. After final liposome formation, the solvent is conveniently removed by continued RO, with addition of several volumes of distilled water.

Figure 3:
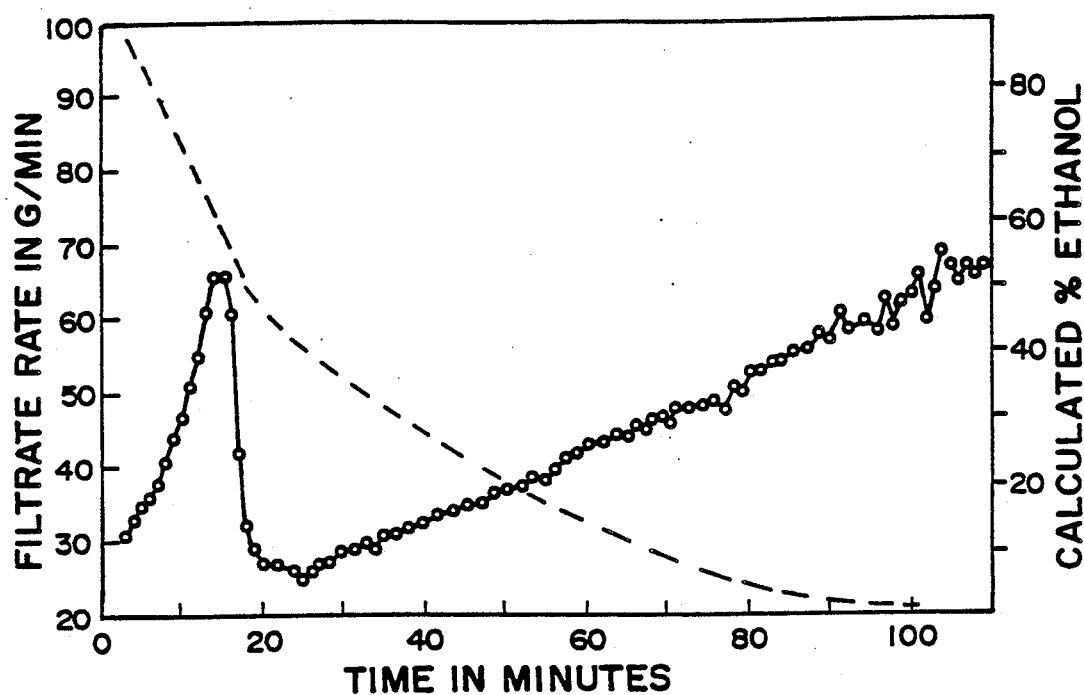
FIG. 3 is a graph of filtration rate (left ordinate) and calculated ethanol concentration (right ordinate), both plotted as a function of filtration time, in a method designed for preparation of liposomes having an average size of about 250 nm.
Figure 4A:
FIGS. 4A–4D are reproductions of photomicrographs of a lipid/solvent/water mixture at increasing water:solvent ratios after initial lipid assembly (4A), at an intermediate stage in liposome formation characterized by heterogeneous size globular lipid structures (4B), during formation of discrete lipid bodies (4C), and after final liposome formation (4D), in the method using reverse osmosis to produce liposomes with an average size of about 250 nm.
Figure 4B:
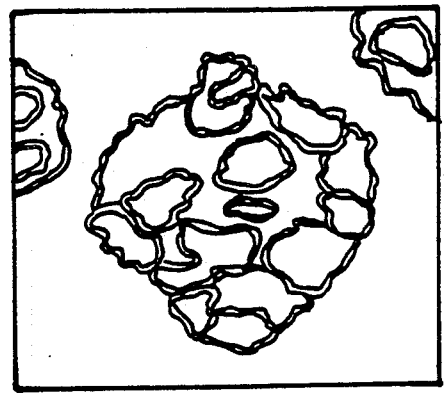
Figure 4C:
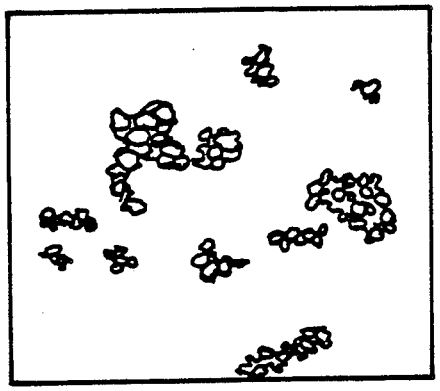
Figure 4D:
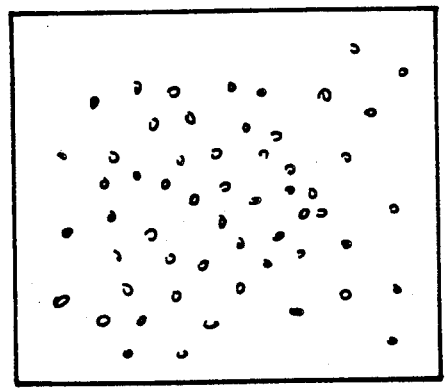

FIG. 3 shows the course of solvent exchange in the liposome-preparation method described in Example 1. Retentate fractions were collected every minute. Flow rate was determined during the course of the method. The filtrate rate, expressed in g/min (left ordinate) is shown in open circles in the figure. Between tubes 6 and 15 (tubes numbered consecutively by time of collection), the appearance of the mixture changed from clear to translucent, but with no indication of liposome formation. The flow rate curve shows a sharp drop at about 16-17 minutes, indicating initial formation of lipid structures, and tubes 16 and 17 showed large lipid aggregates (FIG. 4A). From sample 16 to sample 19, flow rate was substantially constant, as the large lipid structures showed a gradual reduction in size (FIG. 4B). At tube 24, the lipid structures included a mixture of smaller and medium-size vesicles (4C), and by tube 30, the lipid structures had the appearance of the final uniform-size liposomes seen at the end of the solvent exchange (FIG. 4D).

Figure 5:
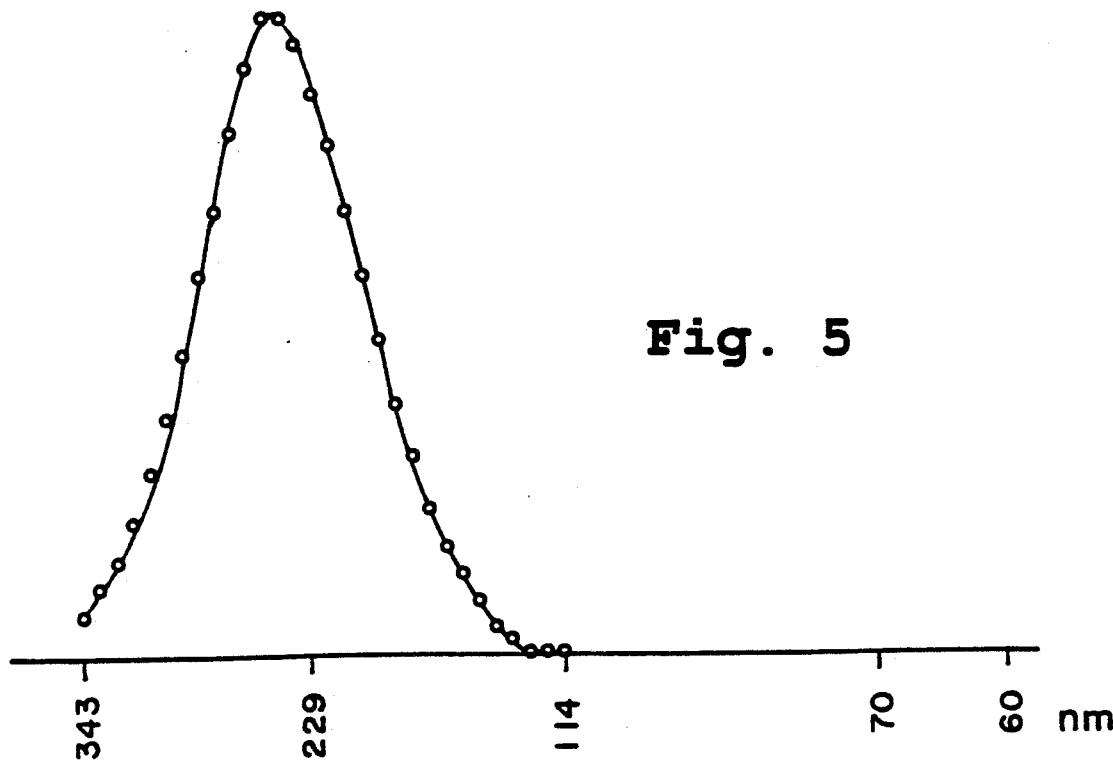
FIG. 5 is a histogram showing the size distribution of liposomes formed in accordance with the method described with reference to FIG. 4.

The dotted line in FIG. 3 shows the ethanol concentration of the collected fractions, calculated on the basis of theoretical dilution in a constant-volume RO system (left ordinate). The first liter of aqueous volume added was supplied as a 158 mM (0.9 M) NaCl solution. At sample 16, when lipid assembly first appeared, about 600 ml of the aqueous medium had been added to the tank, producing a salt concentration of about 95 mM, and an ethanol concentration of about 50%. After the entire 1 liter volume was added (sample 31) an additional 4 liters of distilled water were added, producing a final ethanol concentration of less than 1%. FIG. 5 shows the size distribution of the liposomes formed in the Example 1 method. The size range is from about 110-340 nm and the average size, about 258 nm. As seen, the size distribution of the vesicles is substantially symmetrical about the mean particle size, in contrast to the size distribution of liposomes prepared by liposome sizing methods which involve shear forces on preformed liposomes.

Figure 6:
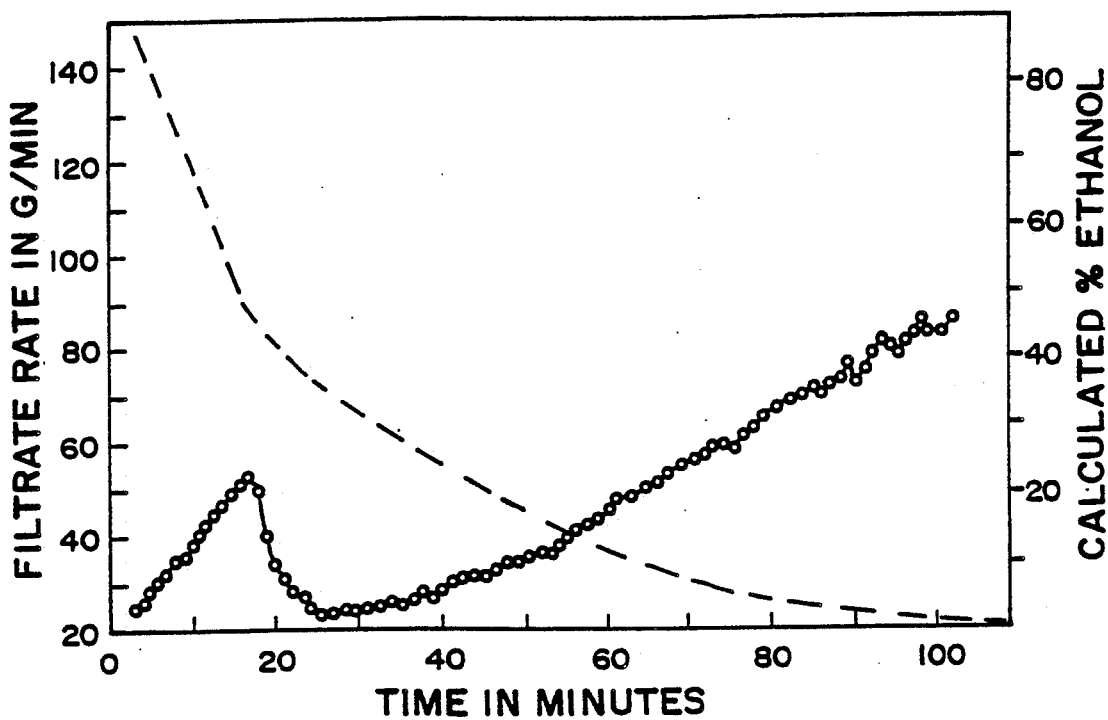
FIG. 6 is a graph of filtration rate (left ordinate) and calculated ethanol concentration (right ordinate), both plotted as a function of reverse-osmosis filtration time, in a method using reverse osmosis to prepare SUVs.
Figure 7:
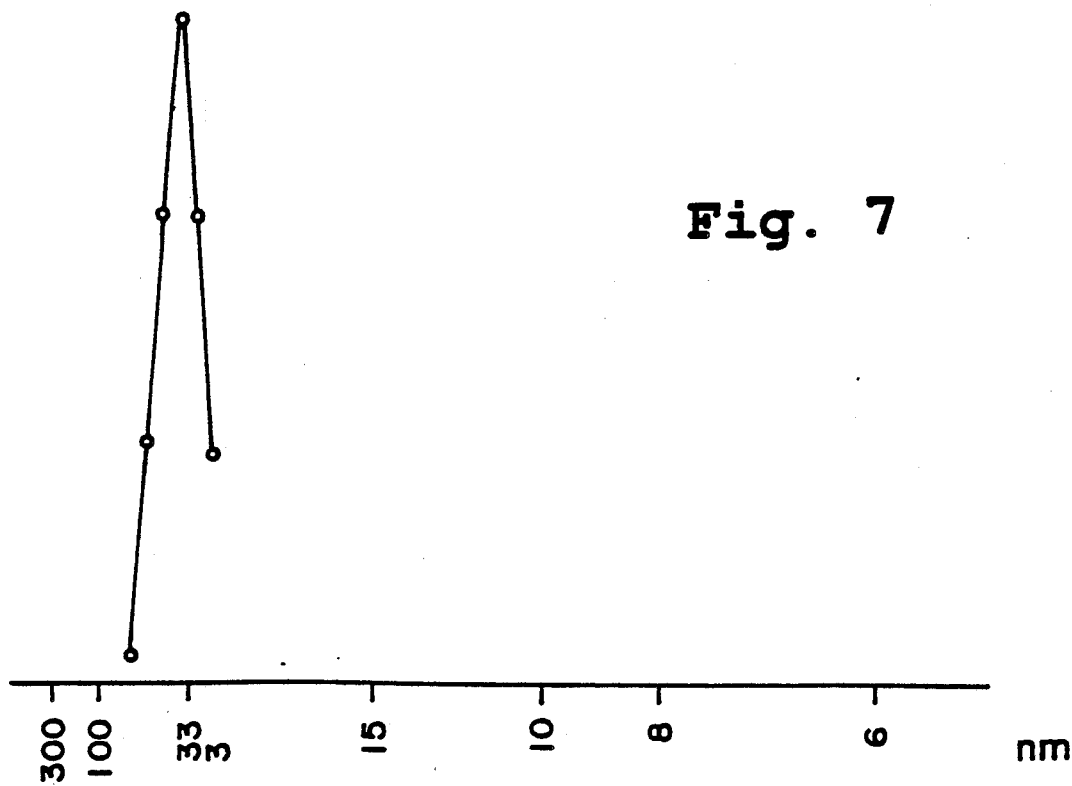
FIG. 7 is a histogram showing the size distribution of liposomes formed in accordance with the method described with reference to FIG. 6.

As indicated above, one aspect of the invention is the ability to control average liposome size, by varying the proportion of charged lipid components and/or ionic strength. The effect of ionic strength can be seen from the RO method described in Example 2. This example is identical to the one in Example 1, except that the ionic strength of the first wash solution is only one-tenth as great, i.e., about 15 mM. FIG. 6 shows the change in flow rate (left ordinate) and calculated ethanol concentration (right ordinate). Flow rate was measured by change in filtrate weight over time. The curves are similar to those shown in FIG. 3. The histogram of liposome sizes, seen in FIG. 7, shows a narrow, substantially symmetrical distribution of sizes between about 30-50 nm, with an average size of about 33 nm.

The lipid mixtures in Examples 1 and 2 both contained 95% egg PC and 5% egg PG, with buffers of varying ionic strengths. The RO method has also been applied to uncharged lipid compositions, e.g., 100% egg PC. The liposomes formed were uniformly sized SUVs, with sizes between about 30-50 nm. Little effect of ionic strength was observed with uncharged lipids.

C. Solvent Exchange by Evaporation

Figure 8:
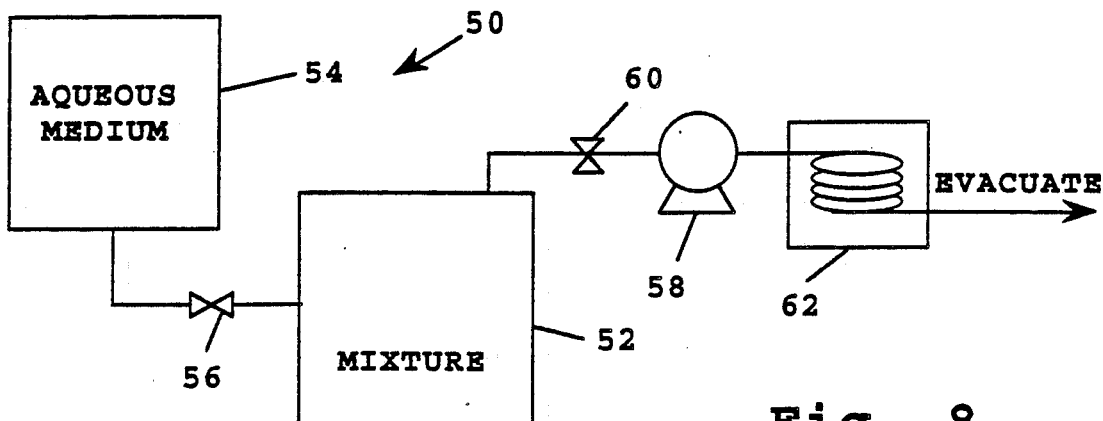
FIG. 8 is a schematic drawing of a solvent evaporation system used in practicing another embodiment of the invention.

FIG. 8 shows a solvent evaporation system 50 designed for solvent exchange according to another embodiment of the invention. The system includes a tank 52 where liposome formation occurs, and a vessel 54 which feeds the aqueous medium to the tank, at a controlled rate, through a pump or valve 56. The pump or valve is adjusted to supply medium to the tank at a rate which balances loss of solvent from the tank.

The reduced pressure in the tank, typically below 1 atm, is produced by vacuum pump 58 which is connected to the tank through a valve 60 used to control pressure. The vacuum preferentially removes solvent in the solvent/water mixture, and this solvent is recovered in a condenser 62. The solvent can also be removed by raising the solution temperature.

As in the RO system, the preferred mixture in the initial stage of operation is a lipid/solvent/water system having a relatively low water:solvent ratio, e.g., 1:10 or less. Thus, the approach to the initial lipid assembly point, as well as the stage between first lipid assembly and uniform-size liposome formation, occurs under substantially constant-volume conditions. The aqueous medium supplied in the method are substantially equivalent to those which would be selected for the RO system. The method yields substantially uniform-size liposomes with a beam diameter value less than about 300 nm.

Figure 9:
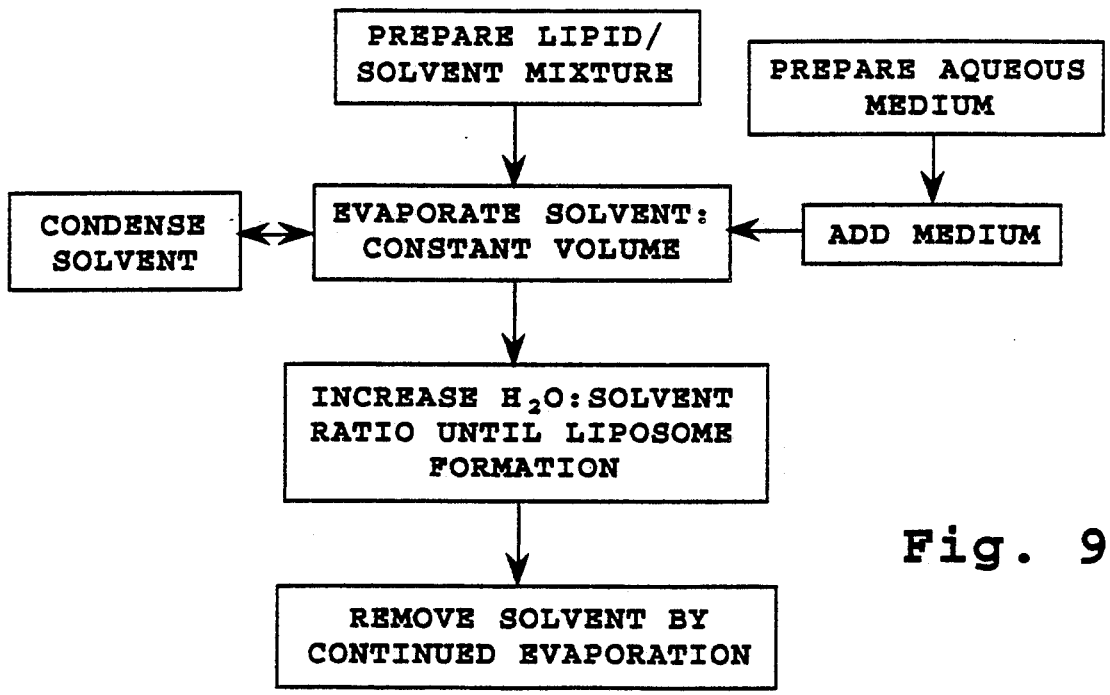
FIG. 9 is a flow diagram of the steps used in practicing the invention using a solvent evaporation system.

FIG. 9 is a flow diagram of the preferred processing steps in the solvent evaporation method. The scheme parallels that used in the RO system. In particular, solvent replacement by evaporation is used to bring the initial mixture to the point of initial lipid assembly, and to raise the water:solvent ratio until uniform-size liposomes form, both under constant volume conditions. Final solvent removal after liposome formation is also performed in the same system.

D. Filter Sterilization and Free-Drug Removal

The uniform-size liposomes may be readily sterilized by passage through a sterilizing membrane having a particle discrimination size of about 200 nm, such as conventional 220 nm depth or membrane filter.

Where liposomes are formulated to contain an entrapped drug, for use in parenteral drug administration, it is often desirable to further process the sized liposomes to remove free drug, i.e., drug present in the bulk aqueous phase of the suspension. Several methods are available for removing free drug from a liposome suspension. The sized liposome suspension can be concentrated by ultrafiltration, then resuspending the concentrated liposomes in a drug-free replacement medium. Alternatively, gel filtration can be used to separate larger liposome particles from solute (free drug) molecules. Ion-exchange chromatography may provide an efficient method of free drug removal, in instances where a suitable drug-binding resin can be identified. One preferred method of free drug removal is by diafiltration, using a conventional hollow fiber or stacked filter device, which preferably has a molecular weight cutoff of between about 10,000–100,000 daltons.

II. Utility

Sized liposome suspensions prepared according to the invention are useful in liposome therapeutic compositions in which controlled sizes less than about 300 nm are desired. One important class of compositions includes drug-containing liposomes for parenteral drug administration. As noted above, liposomal drug-delivery systems have been developed and tested with a wide range of water-soluble and lipid-soluble drugs. Liposomes having a 100 to 300 nm size range are generally preferred to larger-size liposomes, as indicated above, because of ease of sterilization, improved biodistribution, and less tendency to aggregate on storage.

SUVs formed in accordance with the invention are useful in therapeutic applications which involve tumor targeting or infiltration into hepatic cell liver sites. An advantage of SUVs in ophthalmic liposome applications is greater optical clarity. SUVs are also used for producing larger, high-encapsulation liposomes by freeze-thaw methods.

From the above, it can be appreciated that the present invention offers a number of advantages over prior art liposome-sizing methods. The constant-volume processing method is unique in its ability to produce uniform-size liposomes, without the requirement for extrusion or other additional liposome sizing steps. This feature is due at least in part to the substantially constant solvent-/water volume during solvent exchange, which maintains a uniform lipid environment at all stages of liposome formation, and avoids localized lipid dilution effects. This contrasts with earlier-proposed methods in which the water:solvent ratio in a lipid/solvent/water mixture is raised by dilution with water, e.g., as disclosed in EP Patent Application 0,158,441 for "Liposome-Forming Composition", where formation of relatively heterogeneous-size liposomes is observed. The present method also provides for immediate solvent removal, thus lessening encapsulation loss. In addition, the liposomes formed have a significantly more symmetrical size distribution about the mean particle size than has been observed for liposome sizes by prior art methods.

In two preferred processing systems, solvent exchange is carried out under conditions where solvent molecules only are exchanged, and solute molecules, including ionic species, are retained in the mixture. Inherent in these two systems is a uniform-environment solute concentration during liposome formation, since localized solute dilution effects are avoided. Solute retention also minimizes problems associated with solvent recovery and loss of non-encapsulated water-soluble drugs. Since the solute compound is neither lost nor diluted during liposome formation, higher encapsulation efficiencies are possible.

The ability to selectively vary the average size of liposomes, according to lipid composition and/or ionic strength, is another useful feature of the invention. One selected size range, between about 100–300 nm, is advantageous for a variety of parenteral uses, as discussed.

Finally, the invention provides a unique method for forming SUVs, having selected sizes between about 30–80 nm, without shearing-energy input, such as by prolonged sonication or homogenization. Problems of sample contamination, scale-up, oxidative degradation, and extended processing time associated with sonication and homogenization are avoided or minimized. Preliminary studies conducted in support of the invention also indicate that SUVs formed by the present method may have greater size stability on long-term storage than SUVs formed by mechanical shearing.

The following examples illustrate both use and results achievable with the method of the invention, but are in no way intended to limit the scope of the invention.

Materials

Egg phosphatidylcholine (egg PC) was obtained from Lipoid KG, Federal Republic of Germany and egg phosphatidylglycerol (egg PG) was obtained from Avanti Lipids (Birmingham, Ala.). Reverse osmosis membranes, #SK2P473E5, were obtained from Millipore Corp (Bedford, Mass.). A Prolab reverse osmosis (RO) filtration apparatus was obtained from Millipore, Model #MSDPROLAB.

EXAMPLE 1

Preparation of 250 mn Liposomes

Egg PC (38 g) and egg PC (2 g) were dissolved in 473 ml 100% ethanol in a 1 liter flask. After addition of 100 ml distilled water, with stirring, the lipid/ethanol/water mixture was brought to 1 liter with ethanol. The resulting mixture was approximately 50 umole/ml lipid in 90% ethanol.

The mixture was placed in the processing tank of a Prolab filtration apparatus for RO filtration. The RO filter was flushed with an approximately 90% ethanol solution prior to use. The system was run at 80% cross-flow with 500 psi backpressure.

NaCl (9 g) was dissolved in 1 liter of distilled water, and this solution was used as the first aqueous medium, for replacement of ethanol and water lost by RO filtration. Subsequent medium additions were with 4 liters of distilled water. Samples from the process tank were collected every minute. Volume replacement with the five volumes of aqueous medium was complete after about 110 minutes, and the filtration rate varied from about 30 to 60 ml/min during the five-volume replacement. The final concentration of ethanol in the filtered mixture was less than 1%.

The filtrate weight was measured to determine flow rate during the filtration period. FIG. 4 (left ordinate) is a plot of flow rate vs. time (solid circles). The percentage of ethanol in the filtrate (right ordinate) shown in dotted lines in the graph was calculated from theoretical value. At an ethanol concentration corresponding to about 50% ethanol, a sharp decrease in flow rate occurred. This flow gradually increases as the ethanol in the mixture is replaced by water.

To examine the relationship between the formation of lipid structures in the mixture, and the sudden reduction in flow rate observed, samples were taken from the processing tank every minute. Those spanning this portion of the curve were examined by light microscopy. The samples were consecutively numbered by their collection time. Those examined were identified as 6, 12, 15, 16, 17, 18, 19, 20, 24, 30, and 36, where sample 16 corresponds to the peak in filtrate rate. The appearance of samples 16 (FIG. 4A), 19 (FIG. 4B), 24 (FIG. 4C), and 30 (FIG. 4D) are discussed above. No change in liposome appearance was observed after sample 30.

The size distribution of the final liposomes was examined with a dynamic light scattering instrument with Nicomp and Brookhaven correlators. FIG. 5 shows a histogram of liposome sizes. The particles have a mean diameter of 258.5 nm, with a standard deviation of 88.9 and a chi square value of 7.1. No evidence of size change in the liposomes was observed during storage.

EXAMPLE 2

Preparation of 33 nm Liposomes

A lipid/solvent/water mixture containing 95% egg PC, 5% egg PG in 90% ethanol was prepared as in Example 1. The ethanol in the mixture was replaced by RO filtration, as above, except that the initial 1 liter aqueous medium was 0.09% NaCl, rather than 0.9% as used in Example 1. The initial 1 liter aqueous volume was followed by 4 liters of distilled water. One-minute samples of the process solution were taken. Filtrate weight was continuously monitored and used to determine filtrate rate.

FIG. 6 (left ordinate) is a plot of filtrate rate vs. time (solid circles) in the RO procedure, where the calculated percent ethanol is also shown here in dashed line. As above, the RO filtrate rate peaks at about tube 16 or 17, corresponding to about 50% ethanol, declines sharply, then slowly increases as progressively more of the ethanol in the mixture is replaced.

The size distribution of the final liposomes was examined as above, and FIG. 7 shows a histogram of liposome sizes. The particles have a mean diameter of 33 nm, with a standard deviation of 7.1 nm and a chi square value of 6.8.

Although the invention has been described with respect to particular embodiments and uses, it will be appreciated that various changes and modifications may be made without departing from the invention.

It is claimed:

1. A method of forming a suspension of small unilamellar vesicles, comprising forming a mixture of vesicle-forming lipids in a single-phase solvent system comprising a water-miscible lipid solvent and water, at a water/solvent ratio at which vesicular and amorphous lipid structures, visible by light microscopy are formed, and raising the water/solvent ratio, under conditions which maintain a substantially constant volume of the mixture, until uniform-size liposomes are formed, where the lipid composition and ionic strength of the mixture is selected to produce uniform-size liposomes having a mean diameter between about 30 and 80 nm. with a standard deviation of about one-third the selected size range, as measured by dynamic light scattering.

2. The method of claim 1, wherein the vesicle-forming lipids include between 5–10 mole percent negatively charged phospholipid, and the ionic strength of said mixture is between about 5–20 mM.

3. The method of claim 1, wherein the vesicle-forming lipids are neutral phospholipids.

4. A method of forming a suspension of liposomes having a substantially uniform size distribution and a mean diameter of about 300 nanometers or less, comprising preparing a mixture of vesicle-forming lipids in a single-phase solvent system comprising a water-miscible lipid solvent and water, at a water/solvent ratio at which vesicular lipid structures are formed, and raising the water/solvent ratio by adding water to the mixture, and removing solvent preferentially from the mixture by evaporation under reduced pressure, with continued addition of water to maintain the volume of the mixture substantially constant, until uniform-size liposomes having a selected mean diameter of about 300 nanometers or less with a standard deviation of about one-third the selected size range as measured by dynamic light scattering, are formed.

5. The method of claim 4, for use in forming liposomes with an encapsulated, water-soluble compound, wherein said preparing further includes adding the compound to said mixture prior to said raising.

6. The method of claim 4, for use in forming liposomes with an entrapped, lipid-soluble compound, wherein said preparing further includes adding the compound to said mixture prior to said raising.

* * * * *